United States Patent
Génin et al.

(10) Patent No.: US 6,767,550 B1
(45) Date of Patent: Jul. 27, 2004

(54) HYDROXYAPATITE BASED DRUG DELIVERY IMPLANT FOR CANCER TREATMENT

(75) Inventors: François Y. Génin, Berkeley, CA (US); Ping Luo, Berkeley, CA (US); Alekha K. Dash, Omaha, NE (US)

(73) Assignee: Berkeley Advanced Biomaterials, Inc., Berkeley, CA (US)

(*) Notice: Subject to any disclaimer, the term of this patent is extended or adjusted under 35 U.S.C. 154(b) by 0 days.

(21) Appl. No.: 09/608,488

(22) Filed: Jun. 30, 2000

(51) Int. Cl.$^7$ .............................. A61K 9/20; A61F 13/00
(52) U.S. Cl. ...................... 424/426; 424/422; 424/423; 424/424; 424/425; 424/464; 424/472; 424/489
(58) Field of Search .............................. 424/422, 489, 424/423, 424, 425, 426, 464, 472

(56) References Cited

U.S. PATENT DOCUMENTS

| | | | |
|---|---|---|---|
| 5,023,082 A | * 6/1991 | Friedman et al. | 424/426 |
| 5,681,873 A | * 10/1997 | Norton et al. | 523/115 |
| 6,210,715 B1 | * 4/2001 | Starling et al. | 424/489 |
| 6,214,370 B1 | * 4/2001 | Nelson et al. | 424/425 |
| 6,319,512 B1 | * 11/2001 | Rothen-Weinhold et al. | 424/425 |

OTHER PUBLICATIONS

Kunieda et al., Implantation treatment method of slow release anticancer doxorubicin containing hydroxyapatite (DOX–HAP) complex. A basic study of a new treatment for hepatic cancer. Br. J. Cancer (1993), 67, 668–673.*

Uchida A. et al., Slow release of anticancer drugs from porous calcium hydroxyapatite ceramic. Journal of Orthopaedic Research (May–1992); 10(3):440–5.*

Antitumor effects and distribution of adriamycin incorporated into hydroxyapatite implants in a cancer rat models bearing swarm rat chondrosarcoma. Jpn. J. Pharmacol. 66, 443–438 (1994).*

* cited by examiner

Primary Examiner—Thurman K. Page
Assistant Examiner—Simon Oh

(57) ABSTRACT

A hydroxyapatite based bioresorbable material is incorporated with anti-cancer agents to form an implant used for treatment against cancer. Sustained release of the anti-cancer agents may be achieved after implantation at the targeted sites. The dosage of the anti-cancer agent, the microstructure, morphology, and composition of the bioresorbable material allow control of the release profile. The invented implant may be used for drug delivery, chemotherapy, or gene therapy.

9 Claims, 5 Drawing Sheets

Génin et al. "Drug Delivery Implant for Bone or Cartilage Cancer Treatment"

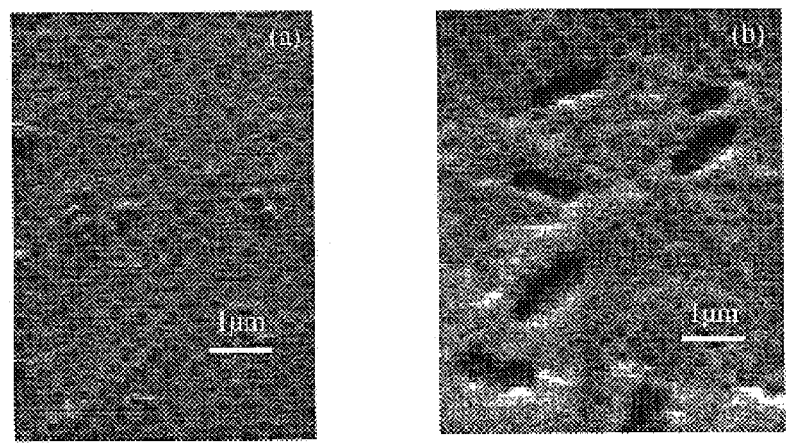
Fig. 1 (a) and (b); Génin et al. "Drug Delivery Implant for Bone or Cartilage Cancer Treatment"

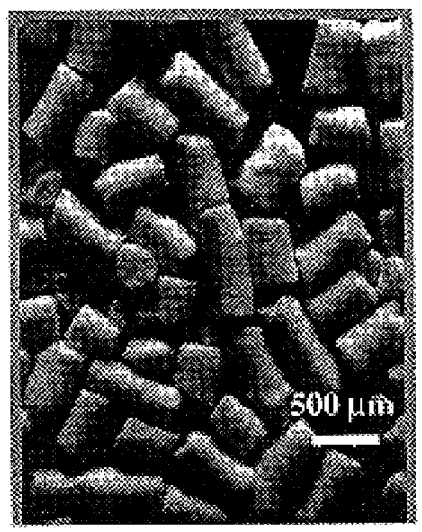
Fig.2; Génin et al. "Drug Delivery Implant for Bone or Cartilage Cancer Treatment"

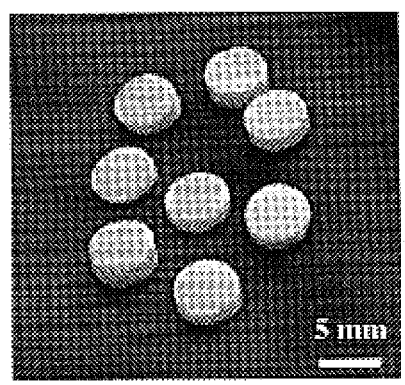
Fig. 3; Génin et al. "Drug Delivery Implant for Bone or Cartilage Cancer Treatment"

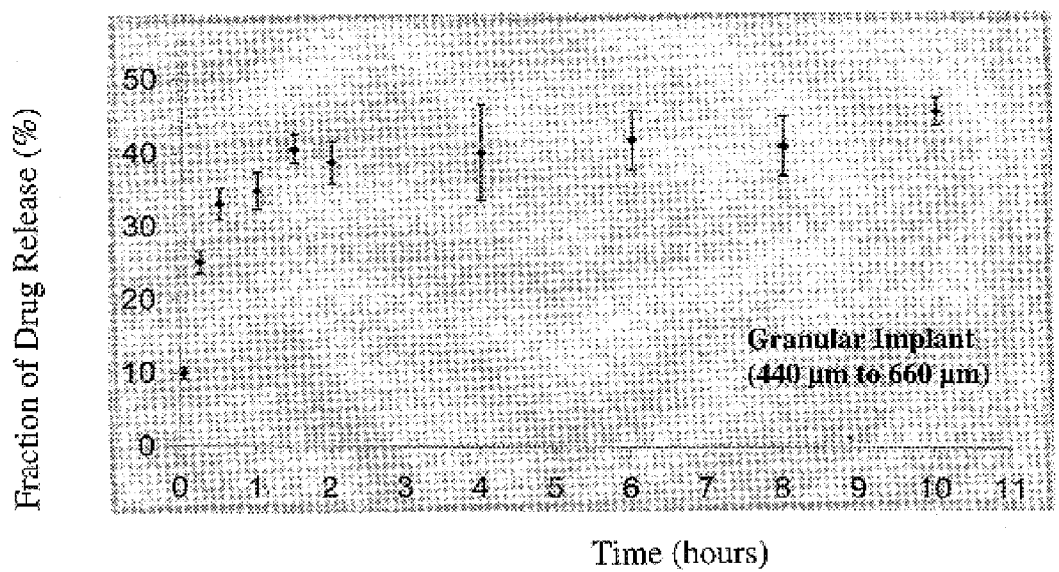
Fig. 4 ; Génin et al. "Drug Delivery Implant for Bone or Cartilage Cancer Treatment"

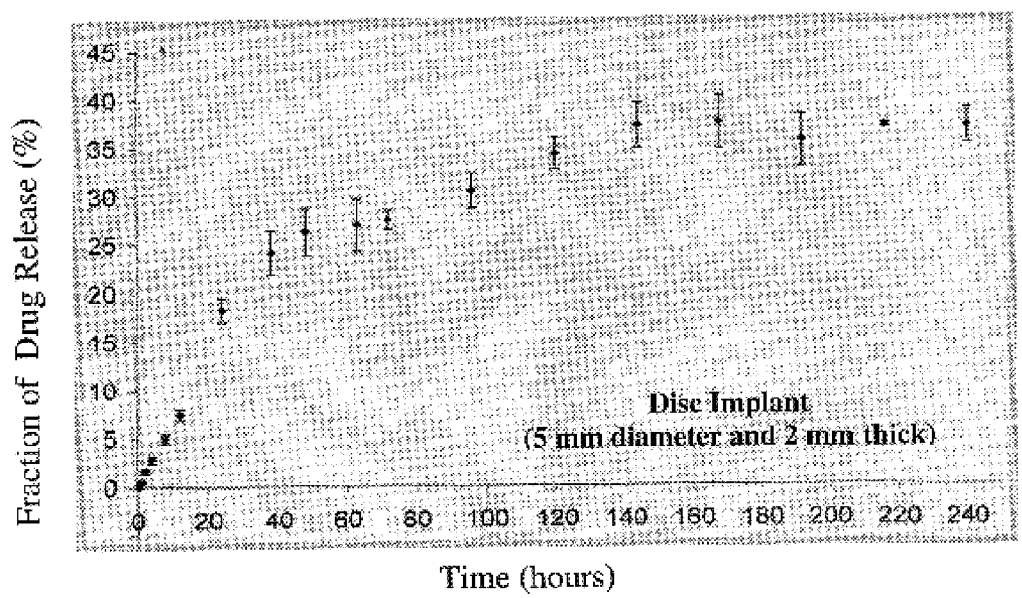
Fig. 5; Génin et al. "Drug Delivery Implant for Bone or Cartilage Cancer Treatment"

HYDROXYAPATITE BASED DRUG DELIVERY IMPLANT FOR CANCER TREATMENT

TECHNICAL FIELD

This invention relates to the composition, preparation and application of drug pre-loaded implant with desired structure and morphology containing anti-cancer agents and pertains to the treatment of cancer. The invented implants provided sustained release profiles after implantation. In this invention, we describe the composition, preparation of granular and disc implants containing doxorubicin. Homogeneous and heterogeneous drug delivery implants with hydroxyapatite and composite biocompatible materials are described. Fabrications of granular implants and disc implants are provided. Sustained release rate measurements of the doxorubicin as an example on the granular implant and the disc implant with a concentration of 0.02% by weight are also provided.

BACKGROUND OF THE INVENTION

Today, drugs are frequently administered orally in liquid or tablet forms. To treat cancer, cytotoxic drugs are used with the object of selective destruction of cancer cells. The major disadvantages of this therapy are their toxic effects on normal cells, and the rapid clearance of the drug from cancerous tissues [Kato, T., in Controlled Drug Delivery, Vol. 11, Clinical Applications, ed. Bruck, S. D., CRC Press, Boca Raton, Fla., (1983) pp. 189–240]. To avoid problems incurred through the use of oral drugs, new dosage forms containing the drugs are introduced. There is a significant advantage to producing drug delivery systems that can maintain a constant drug release rate and can release the drug locally at the specific site of action. Therefore, implantable drug delivery systems were developed to optimize the therapeutic properties of the drug products and render them safer, more effective, and reliable. The advantages of drug delivery implants over conventional oral drugs are that:

1. a lower drug dose is needed,
2. the drug is protected from rapid in vivo metabolism,
3. the effectiveness of the drug at the site of the action is increased,
4. the patient compliance is increased and,
5. the delivery can continue over a period of time that can last for five years while requiring only minimum monitoring.

Methods of treating bone or cartilage cancer:

One of the important and effective drugs for treating osteosarcoma which is the most prevalent form of bone cancer is doxorubicin [Marsoni, S., Hoth, D., Simon, R., et al., Clinical Drug Development: An analysis of phase II trials, 1970–1985, Cancer Treat. Rep. 71, (1987) 71–80]. Since doxorubicin has poor oral absorption, it is administered intravenously. In the treatment of bone cancer, the problems associated with intravenous doxorubicin administration are: (i) toxicity of the drug; and, (ii) drug concentration at the cancerous site is likely to be very low because bones in general are moderately perfused organs. Administration of a 30 mg/m$^2$ of doxorubicin as an intravenous bolus dose resulted to a marro drug concentration of 0.52 $\mu$g/g, 2.5 hours after administration [Cohen, J. L., and Chan, K. K., in Bone Metastatsis Eds. Weiss, L. and Gilbert, H., A., Hall Medial Publishers, Boston, Mass., (1981) pp. 276–299]. Cardiotoxicity is the major chronic toxicity of doxorubicin and is dose-dependent [Sadee, W. and Torti, F. M., in Fundamentals of Cancer Chemotherapy, eds. Hellmann, K. and Carter, S. K., McGraw-Hill, New York, N.Y., (1987) pp. 19–27]. A cumulative dose of 700 mg.m$^2$ causes 30–40% of the patients to experience cardiotoxicity.

The treatment of bone cancer in most cases involves surgical intervention followed by systemic chemotherapy. This therapy, commonly referred to as adjuvant chemotherapy, is used to eradicate microscopic foci of metastatic disease. Ettiger et al. used a combination of doxorubicin and cisplatin as adjuvant therapy to treat osteosarcoma patients. Eighty percent of their patients were continuously disease-free for 23 months [Ettiger, L. J., Douglas, H. O., Higby, D. J., et al., Adjuvant adriamycin and cis-diammine-dichloro-platinum in promary osteosarcoma, Cancer 47, (1981) 248–254]. Rosen et al. developed a very unconventional but successful treatment protocol which involved the following sequential steps: (i) a regimen of systemic chemotherapy initiated several weeks before surgery; (ii) resection of enoprosthetic replacement of tumor-bearing bone rather than amputation; (iii) histologic examination of resected primary tumor to evaluate the effect of the preoperative chemotherapy; and, (iv) initiation of a new postoperative chemotherapeutic regimen, if preoperative chemotherapy regimen was not effective [Rosen, G., Capparros, B., Huvos, A. G., et al., Preoperative chemotherapy for osteogenicsarcoma: selection of postoperative adjuvant chemotherapy based on the response of the primary tumor to preoperative chemotherapy, Cancer, 49(1982) 1221–1230].

This mode of treatment showed that 93% of the patients had been continuously disease free for 20 months. However, the systemic toxicity of doxorubicin was a cause for concern in some patients.

Objective and Disclosure of the Invention

The first objective of the present invention is to provide implants that can deliver drugs, proteins, peptides, DNA molecules, and hormones for treating bone or cartilage cancers. The second objective is to design the composition of the anti-cancer agents and the morphology of the biocompatible matrix materials to achieve the desired release rate profile for therapeutic treatment. The third objective is to provide methods for preparing of the foregoing implants.

As will become apparent, preferred features and characteristics of one aspect of the invention are applicable to any other aspects of the invention.

In one aspect, the invention provides a method for treating bone or cartilage cancer using hydroxyapatite drug delivery implants.

In a preferred embodiment, the drug delivery implant includes either a single-phase hydroxyapatite or multi-phase calcium phosphates. In another preferred embodiment, the hydroxyapatite can be amorphous or crystalline. In another preferred embodiment, the phase of the calcium phosphate can be alpha-tri-calcium phosphate or beta-tri-calcium phosphate. In other preferred embodiments, the drug delivery implant is composed with at least one biocompatible material such as biocompatible polymer, collagen, bioactive glass, calcium sulfate, carbonate apatite, fluoroapatite, or a biocompatible apatite phase.

In another preferred embodiment, homogeneous or heterogeneous implants are prepared by controlling the composition of anti-cancer agents, the biocompatible materials and the pressing process. In another preferred embodiment, the pressure applied to form the granular, disc, tablet, or block implants ranges from 0.1 to 40 MPa.

In another preferred embodiment, the invention includes using 0.02 weight percentage of doxorubicin to hydroxyapatite to obtain a sustained release.

In another preferred embodiment, the invention includes mixing doxorubicin and hydroxyapatite to form granular implants in a cylindrical shape. The diameter of the cylinder ranges from 5 microns to 10 millimeters.

In another preferred embodiment, the invention includes mixing doxorubicin and hydroxyapatite to form tablet or disc implants. The diameter of the tablet or disc ranges from 4 millimeters to 100 millimeters.

In another preferred embodiment, the invention essentially involves introducing granular and disc implants containing doxorubicin into the tumor or in its vicinity.

BRIEF DESCRIPTION OF THE DRAWINGS

FIGS. 1(a) and 1(b) contains two scanning electron micrographs, which reveal the typical surface microstructure of homogeneous and heterogeneous implants containing doxorubicin; FIG. 1(a) low concentration and FIG. 1(b) high concentration.

FIG. 2 is an optical micrograph of cylindrical-shaped granular implants.

FIG. 3 is an optical micrograph of disc-shaped implants.

FIG. 4 is an in vitro release profile of granular hydroxyapatite-doxorubicin implants FIG. 5 is an in vitro release profile of disc hydroxyapatite-doxorubicin implants.

SUMMARY OF THE INVENTION

We have invented a novel method to deliver anti-cancer agents in desired concentrations, wherein the dosage form, which anti-cancer agents such as doxorubicin are incorporated into a biocompatible matrix material, is an implant. The therapeutic method includes administering the drug topically, systemically, or locally as an implant or device. The drug is preferably used for bone or cartilage cancer treatment. The implant can be directly placed within or around the bone or cartilage adjacent to the tumor. This mode of treatment has the following advantages:
1. rapid reduction in the mass and size of primary tumors; this could increase the possibility of organ-salvage surgery and thereby accelerate patient rehabilitation after surgery),
2. decreased likelihood of metastasis after initiation of treatment because of the rapid reduction in the number of tumor cells,
3. virtual elimination of the systemic side effects because of the smaller dose used and its confinement to a local site.

Human bone is known to contain on average about 70% minerals. The minerals are in majority composed of hydroxyapatite, carbonate apatite, and calcium phosphates. Fluoroapatite has also been reported to occur in bones such as teeth. The biocompatible materials described in this invention include any bioresorbable materials such as collagen, calcium sulfate, bioactive glass, bioresorbable polymer, single-phase hydroxyapatite or multiphase calcium phosphates (crystalline or amorphous). The choice of the biocompatible matrix is determined to control the resorption rate of the implant and the release rate of the anti-cancer agent. Clinical studies proved that bioresorbable materials promote bone growth. The porosity of the implant improves osteo-conduction and osteo-induction. The resorption rate can be tailored by controlling the degree of crystallinity, the microstructure, and the morphology of the implant. The implant can be fully resorbed after a period of time that can range from 2 weeks to 24 months.

Many anti-cancer agents can be incorporated into biocompatible materials to form the implant. Among the anti-cancer agents available today, the most effective for treating bone cancer is doxorubincin. The implant can be used for targeted chemotherapy. The implant can be surgically placed at or around the tumor site or within the bone directly adjacent to the tumor. After implantation, the anti-cancer agents are released continuously or periodically from the implant at a desired rate. Periodical release can be achieved with for example a multi-layered tablet of pure hydroxyapatite and hydroxyapatite loaded with anti-cancer agents. The anti-cancer molecules then approach the tumor cells preferentially as a result of their proximity.

Several therapeutic delivery systems were developed and patented. Unger et al. describe in U.S. Pat. No. 5,542,935 a system comprising of gaseous precursor-filled microspheres, in which doxorubicin are encapsulated.

In U.S. Pat. No. 5,656,108, Nies et al. describe a process to prepare porous bone replacement materials composed mainly of acrylate/methacrylate. Hydroxyapatite particles are used as an additive and are not in excess of about 30% by weight. Active compounds such as doxorubicin are added to the constituents of bone cements and hardened to form an implant. In the present invention, the biocompatible material such as hydroxyapatite is greater than 70% by weight, which is the main phase of the drug delivery implant.

In U.S. Pat. No. 5,797,873, Franz et al. describes a process to prepare bone cements comprising of active compounds including doxorubicin. The bone cement is composed of a solid component and a liquid component. The solid component is about 50% to 75% by weight. The active component is dissolved into an organic solvent. Hydroxyapatite is used as an additive.

In U.S. Pat. No. 5,968,253, Poser et al. describe a process to prepare calcium phosphate cements comprising antimicrobial agents. A flowable compound containing calcium phosphates and a liquid lubricant loaded with anti-microbial agent becomes an apatitic product such as hydroxyapatite after injection into the body. The anti-microbial agents are from the group consisting of gentamycin and vancomycin.

Other drug delivery systems have been invented to treat bone infections. U.S. Pat. No. 5,514,137, by Coutts describes an orthopedic device made of a cement composed of hydroxyapatite, ortho-phosphoric acid, calcium carbonate, and calcium hydroxide. The cement material contains an active agent selected from the group consisting of antibiotics, bone growth promoters, vasoactive agents, and other drugs to prevent or mitigate infection. U.S. Pat. Nos. 5,939,380, and 5,110,595, by Wang describes a process of producing implants containing bioactive macromolecules for sustained delivery. A lipid powder is mixed with bioactive polypeptides and compressed into disc or rod-shaped implants. This polymer based drug delivery implant is mixed with insulin, which is a polypeptide hormone, with a concentration of up to 40% by weight. This type of device can hold a sufficient amount of active proteins to sustain the desired therapeutic effect for many weeks.

Further, in U.S. Pat. No. 5,780,044, Yewey, et al, described biocompatible liquid delivery compositions, which provide sustained release of active agents. The liquid delivery compound consists a biocompatible polymer or prepolymer in combination with an active agent such as doxorubicin. The liquid delivery system may be introduced into the body and it solidifies or cures in situ to form a controlled release implant or a film dressing. The liquid delivery compound may also be employed ex situ to produce a controlled release implant.

Various types of drug delivery systems formulated with anti-cancer agents include drug-antibody complexes, albumin microspheres, ferromagnetic or ethyl cellulose microcapsules, biodegradable micro-capsules, and liposomes [Kato, T., in Controlled Drug Delivery, Vol. 11, Clinical Applications, ed. Bruck, S. D., CRC Press, Boca Raton, Fla., (1983) pp. 189–240 and Davigonon, J. P. and Craddock, J. C., in Fundamentals of Cancer Chemotherapy, eds. Hellmann, K. and Carter, S. K., McGraw-Hill, New York, N.Y., (1987) pp. 212–217]. Most of these dosage forms have been formulated for parenteral administration. Although these drug delivery systems have found a variety of uses in targeting certain forms of cancer, their suitability to treat bone cancer has not yet been demonstrated.

Polydimethylsiloxane (PDMS) is an inorganic synthetic and biocompatible polymer that is used popularly as a drug delivery matrix. The medical-grade silicone is prepared from PDMS. It has been successfully used in sustained- and controlled-release drug delivery systems. The release rate of lipophilic drugs such as progesterone and testosterone from silicone polymers is several orders of magnitude higher than from organic polymers. However, the release rate of hydrophilic drugs incorporated into silicone implants is very low. The addition of some hydrophilic compounds, such as glycerol, to the polymer matrix greatly enhances the release rate of several hydrophilic drugs. Unfortunately, the shelf-life of such implantable drug delivery system is short due to the instability of the polymer matrix with the addition of glycerol [Dash, A. K. and Suryanarayanan, R. (1992) An implantable dosage form for the treatment of bone infections. Pharm. Res. 9: 993–1002].

Implantable biodegradable polymer (Poly-lactic-glycolic acid) micro-capsules containing gentamycin and ciprofloxacin have been prepared and evaluated in the treatment of osteomyelitis [Sampath, S. S., Garvin, K. and Robinson, D. H. (1992) Preparation and characterization of biodegradable poly(lactic/glycolide) (50:50)-gentamycin delivery systems. Int. J. Pharm. 78:174 and Ramehandani, M. and Robinson, D. H. (1998) In vitro and in vivo release of ciprofloxacin from PLGA 50:50 implants, J. Control. Rel. 54:167–175]. The advantage of this approach is that the dosage form needs not be removed from the body at any time. Resorption of the implant was observed to occur in 6 to 8 weeks, which is longer than expected. Sub-therapeutic concentrations of antibiotics in the bone for an extended time period could also lead to the development of resistant organisms. Moreover, prolonged exposure to the antibiotics could lead to hypersensitivity reactions [Schurman, D. J., Trindade, C., Hirshman, H. P., Moser, K., Kajiyama, G. and Stevens, P. Antibiotic-acrylic bone cement composites: studies of gentamycin and Palacos. J. Bone. Joint Surg. 60A, (1978), pp. 978–984]. More importantly toxic organic solvent like methylene chloride is generally used for their complex fabrication procedure.

Hydroxyapatite, tri-calcium phosphate, and amino acid antibiotic composite ceramics are some of the most biocompatible and bioresorbable synthetic hard tissue implant materials. When they are combined with amino acids in water, the resultant formulation provides a composite which sets with similar consistency to cement that is free of both local and systemic toxicity. They directly bond to bone via natural mechanisms, thus allowing for utilization to stabilize traumatized bone fractures. When loaded with antibiotics, such systems can also release the drug at therapeutic concentrations directly to the infected area [Morris, L. and Bajpai, P. K., Development of a resorbable tri-calcium phosphate amine antibiotic composite in biomedical materials and devices, Eds. Hanker, J. S. and Giammara, Pittsburgh, Pa.: Materials Research Society, (1989) pp. 293–300]. Hydroxyapatite and tri-calcium phosphates containing cysteine or lysine composites loaded with erythromycin or penicillin have been developed for the treatment of bone infections. The results revealed that a constant release of antibiotics was obtained over a period of 3 weeks at the site of infection. This study suggests that antibiotics released from tri-calcium phosphate amino acid composites can be effectively utilized in the treatment of bone infections.

The implant of this invention is capable of releasing the anti-cancer agent over the entire period of resorption. To achieve a fast resorption rate, calcium sulfate and amorphous or nanocrystalline hydroxyapatite drug delivery carriers are excellent candidates. On the other hand, bioactive glass is more suitable to achieve slow resorption rates. A mixture or a multi-layered structure of pure and drug-loaded biomaterials can form an implant for which the resorption rate is designed.

The release rate and release profile can be tailored by the morphologies of the biocompatible implant in this invention. The results of the in vitro release tests in examples 1 and 2 for hydroxyapatite granules and discs respectively showed that the granular implants release doxorubicin much faster than the disc implants (see FIGS. 3 and 4). More complex release profiles can be obtained from mixtures of implants with different microstructures and geometry.

The implants may be heterogeneously or homogeneously mixed with the bio-molecules depending on their concentration, the composition of the biocompatible materials, and the implant processing pressure. The two typical surface structures obtained are shown in FIG. 1.

The implants may be dense or porous. Porous implants provide pathways for fast diffusion and lead to quicker delivery than dense implants. The pore sizes of porous implants can be tailored from 1 micron to 3 mm depending on the desired release profiles.

Anti-cancer agent incorporation into an implant is achieved by dissolving the agent in water or solvents and mixing it with the biocompatible materials such as hydroxyapatite powder to form a slurry. The slurry can then be dried into granular implant with desired shapes using a large variety of commercially available equipment, such as a spray dryer, a vacuum dryer, or a fluidized bed. The drying temperature ranges from room temperature to 150° C. to avoid decomposition of the anti-cancer agent. In U.S. Pat. No. 5,858,318, Luo, P. described a process producing hydroxyapatite microspheres, hollow spheres, and doughnut-shaped particles by controlling the spray drying parameters. A foaming agent e.g. ammonium hydroxide was co-sprayed to form interconnected micropores.

In addition, the slurry can be dried into a paste and then formed into desired shapes by casting methods. The granular implant in this invention is formed into a cylindrical shape (see FIG. 2). The diameter of the cylinder depends on the size of hole on the mold. Furthermore, the paste can be injected with a foaming agent into a mold with desired geometry such as square, rectangle, disc, cylinder, and sphere. The concentration of the foaming agent and the process temperatures control the pore size of the block implant.

A simple method can be used to form block implants using a press and dies with different diameters. Biocompatible binding agents can be used to form the disc implant if low pressures are applied.

The block implant can be incorporated homogeneously or heterogeneously with the anti-cancer agent. Homogenous implants can be obtained by loading a low concentration of the anti-cancer agent. Forming into desired shapes at various pressures and mixing with biodegradable polymers such as collagen, gelatin, and polymer in various compositions can also result in a homogenous implant.

A method to use the implant material of this invention is also provided. To demonstrate the method, the hydroxyapatite drug delivery implant is implanted surgically within the bone or the cartilage either into the tumor or around it. The implant can be placed in the void after a tumor is removed to continue treatment therapeutically. Since hydroxyapatite is osteoinductive and osteoconductive, the void can be replaced by new bone after the completion of the release and the resorption of the implant.

The term "bioresorbable materials" refers to a group of materials that have been shown to clinically resorb in the human body. The bioresorbable materials in this invention include calcium phosphates, hydroxyapatite, apatites, calcium sulfates, bioresorbable polymers, collagen, gelatin, and bioactive glass. Calcium phosphates include alpha-tri-calcium phosphate and beta-tri-calcium phosphate.

The term "anti-cancer agents" includes all bioactive agents that can kill or inhibit the growth of cancer cells. This includes proteins, peptides, DNA molecules, and hormones, which can be incorporated into the implant to increase the delivery efficacy and treat against cancer. The concentrations of the incorporation range from 0.0001% to 30% by weight. The anti-cancer agents diffuse out of the body of the implant into the targeted site.

The term "desired release profile" means that the release profile can be tailored by controlling the concentration of the anti-cancer agents, the microstructure, and the morphology of the implant.

The term "granular implant" refers to drug delivery implants that have the morphology of granules. The size of the granules ranges from 5 microns to 10 millimeters.

The term "disc implant" refers to a drug delivery implant that has the morphology of a disc.

The term "block implant" refers to a group of drug delivery implants that have morphologies of squares, rectangles, discs, cylinders, spheres, or irregular shapes.

EXAMPLE OF THE INVENTION

Example 1

Fabrication of granular implants

Doxorubicin was dissolved into distilled and debacteried water to a concentration of 2 mg/ml at room temperature. Dried hydroxyapatite powder was then mixed with the 0.02 wt % doxorubicin solution to form a slurry. The slurry is then transformed into a paste. The paste is extruded into cylindrical granules with an average size of 500 μm. Optical microscopy reveals that the surface of the implant is smooth (see FIG. 2).

In vitro release studies 25 mg of granules in 40 mL medium were used for the release study. The granules were placed in a polypropylene flask containing 40 ml of 0.05 N Tris buffer (pH 7.4). The flask was agitated at 80 rpm by the Precision reciprocal shaking water bath at 37±1° C. At definite time intervals, 0.5 ml of the released medium was collected and replaced with 0.5 ml of fresh buffer. In vitro release studies were carried out in triplicates. The doxorubicin content in the release medium was determined by HPLC.

The release profile for granules is shown in FIG. 4. The doxorubicin released about 40% fraction after 10 hours.

Example 2

Fabrication of Disc Implant

Disc implants were formed by pressing pure hydroxyapatite powder with doxorubicin. Neither binding agents nor foaming agents were used in this example. A pressure of 6 MPa was applied to form 5-mm diameter and 2-mm thick discs (see FIG. 3). The implants contain 0.02 wt % doxorubicin.

In Vitro Release Studies

The procedure described in example 1 was followed to determine the release profile of the disc implant. A 25-mg disc implant was placed into 40 mL of test medium. As seen in FIG. 5, a fast release of doxorubicin from the disc implant is initially observed. The release slowed down after 40 hours (see FIG. 5). The release of the doxorubicin reached a 35% fraction and lasted for 240 hours. Sustained release was achieved on the disc implant. This profile demonstrates the potential therapeutic use of drug delivery disc implants for treating bone and cartilage cancer.

What is claimed is:

1. A two layered, sustained release, biocompatible implant comprising a first layer consisting of pure hydroxyapatite and a second layer comprising hydroxyapatite, a bioresorbable material, and doxorubicin homogeneously distributed in amounts from 0.0001 to 30% by weight.

2. The biocompatible implant of claim 1, wherein said implant is a tablet, disc, or cylindrical granular implant.

3. The biocompatible implant of claim 1, wherein said implant is injectable and moldable.

4. The implant of claim 1, wherein the first layer further comprises a material selected from the group consisting of one or more calcium phosphates, calcium sulfate, carbonate apatite, fluoroapatite, bioactive glass, biodegradable polymers, collagen, and gelatin.

5. The implant of claim 1, wherein resorbtion lasts from 2 weeks to 4 years.

6. The implant of claim 1, wherein said implant is either porous or dense.

7. The implant of claim 1, wherein the first layer and second layer is either porous or dense.

8. The implant of claim 1, wherein the implant is introduced within bone adjacent to a tumor, around a tumor, inside a tumor, or within the void after a tumor is removed.

9. The implant according to claim 2 having a size ranging from 5 microns to 10 mm.

* * * * *